(12) United States Patent
Kinigakis

(10) Patent No.: US 6,511,726 B1
(45) Date of Patent: Jan. 28, 2003

(54) FLAVOR RETENTION AND RELEASE SYSTEM

(75) Inventor: Panagiotis Kinigakis, Mount Prospect, IL (US)

(73) Assignee: Kraft Foods Holdings, Inc., Northfield, IL (US)

(*) Notice: Subject to any disclaimer, the term of this patent is extended or adjusted under 35 U.S.C. 154(b) by 64 days.

(21) Appl. No.: 09/672,156

(22) Filed: Sep. 27, 2000

(51) Int. Cl.$^7$ ................................................. B65D 85/72
(52) U.S. Cl. .................... 428/40.1; 215/341; 215/347; 215/348; 239/6; 239/55; 239/56; 239/60; 428/40.9; 428/41.1; 428/41.3; 428/41.7; 428/41.9; 428/42.1; 428/137; 428/138; 428/192; 428/318.4; 428/319.7
(58) Field of Search .................... 428/40.1, 40.9, 428/41.1, 41.3, 41.7, 41.9, 42.1, 137, 138, 192, 318.4, 319.7; 215/341, 347, 348; 239/6, 55, 56, 60

(56) References Cited

U.S. PATENT DOCUMENTS

| | | | |
|---|---|---|---|
| 2,241,022 A | 5/1941 | Sierad et al. .................. 215/38 |
| 3,685,734 A | 8/1972 | Paciorek et al. .............. 239/56 |
| 4,634,614 A | 1/1987 | Holzner ........................ 428/35 |
| 4,990,345 A | 2/1991 | Webb ........................... 426/123 |
| 5,011,019 A | 4/1991 | Satoh et al. ................. 206/530 |
| 5,071,704 A | 12/1991 | Fischel-Ghodsian ........ 428/354 |
| 5,249,676 A | * 10/1993 | Ashcraft ...................... 206/264 |
| 5,518,790 A | 5/1996 | Huber et al. ................. 428/352 |
| 5,542,557 A | 8/1996 | Koyama et al. ............. 215/347 |
| 5,635,229 A | 6/1997 | Ray ............................. 426/112 |
| 5,804,264 A | 9/1998 | Bowen ....................... 428/35.2 |
| 5,885,630 A | 3/1999 | Zurawski et al. .............. 426/5 |
| 5,934,494 A | 8/1999 | Takahashi et al. ........... 215/347 |

OTHER PUBLICATIONS

PCT International Search Report, International Application No. PCT/US01/29495, dated Jan. 2, 2002.

* cited by examiner

Primary Examiner—Nasser Ahmad
(74) Attorney, Agent, or Firm—Fitch, Even, Tabin & Flannery

(57) ABSTRACT

A system for retaining and releasing an active compound, such as a volatile flavor oil is provided. A storage layer of foam is located between layers of diffusion material which are extrusion coated onto the storage layer. A barrier layer, such as a foil material, is peelably bonded to the film layer on one side of the storage layer. The resulting composite is adhesively secured to a closure, such as a container cap, and remains with the cap. The foil layer is fixedly bonded to a container and remains with the container after the closure is removed by a consumer. With removal of the foil layer and subsequent openings and closings to obtain product within the container, new concentrations of the active compound are created within the container head space and are available for a substantial aroma impact upon subsequent opening.

14 Claims, 2 Drawing Sheets

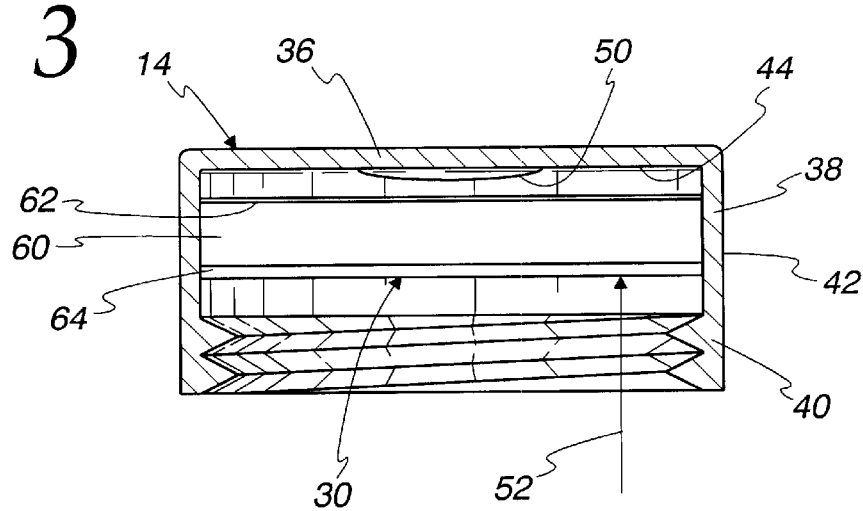
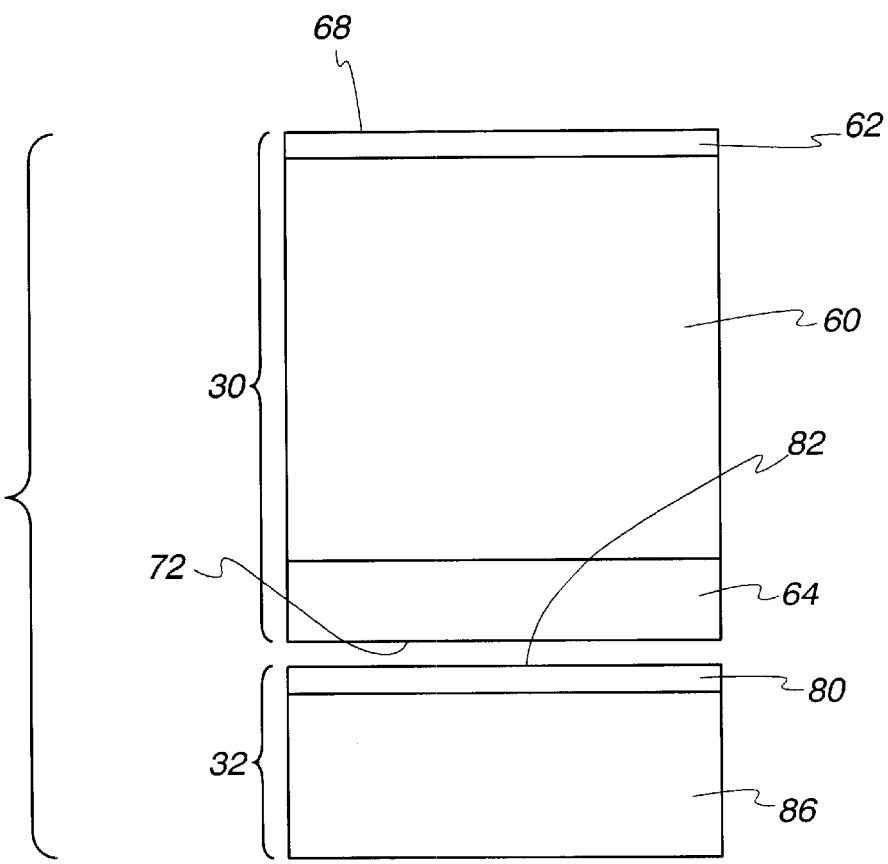

FLAVOR RETENTION AND RELEASE SYSTEM

BACKGROUND OF THE INVENTION

1. Field of the Invention

The present invention pertains to systems for retaining and releasing active compounds, especially volatile flavors used in conjunction with products shipped in sealed containers.

2. Description of the Related Art

Several types of volatile flavor (or fragrance) release systems have been employed in a commercial context. For example, samples of perfumes or other commercial fragrances are stored in a literary magazine, usually associated with an accompanying advertisement. When the magazine page is opened, a sample of the fragrance is released. Unfortunately, once the magazine page is opened, the fragrance is quickly dissipated. Increasing the dose of fragrance agent may not offer a practical solution, since the initial fragrance experienced by a potential customer is rendered unusually strong.

Other areas of commercial endeavors have sought to obtain the benefit of fragrance enhancements. For example, consumers typically have a strong association of fragrance with certain commercial products, such as coffee. New and innovative coffee products may not have the level of fragrance expected and accordingly, efforts have been made to add fragrance directly to an otherwise successful coffee product.

For example, commercial packaging of instant coffee is augmented by adding an oil base of coffee flavor concentrate directly in the granular instant coffee product. The granules of the instant coffee absorb the oil concentrate and, once the container is sealed, the volatile flavor fills the container head space. Depending upon a number of factors, the release of volatile flavors when the consumer first opens the package may or may not provide the desired impact of aroma. Beyond this, the volatile aroma will be quickly lost after the first opening of the container since the dilution of the head space by the ambient atmosphere will not be overcome with subsequent re-sealing of the container. It is desirable to provide a sustained release of volatile flavors following the first opening of the container, and to extend the fragrance experience until the container is emptied.

SUMMARY OF THE INVENTION

It is an object of the present invention to provide a controlled, prolonged release of an active agent, such as a volatile flavor, after an initial opening of the container and upon successive re-openings, thereafter, Another object of the present invention is to provide a controlled flavor retention and release system for volatile flavor agents and other active agents which is compatible with commercial methods for filling and sealing containers holding a commercial product, and in particular a commercial food product.

A further object of the present invention is to provide a flavor retention and release system that reduces scalping of volatile flavors using a closure system compatible with existing commercial packaging, and which can be constructed from a minimum number of inexpensive parts.

These and other objects according to principles of the present are provided in a flavor retention and release system for use with a container having an opening enclosed by a closure releasably engageable with said container, comprising:

a permanent liner assembly dimensioned to be received in said closure, so as to cooperate therewith to form a pocket for retaining a volatile flavor agent;

a permanent bond bonding at least a portion of said permanent liner assembly to said closure;

a removable liner including a diffusion barrier impermeable with respect to said flavor agent;

a container bond bonding said removable liner assembly to said container;

a releasable bond, releasably bonding said removable liner assembly to said permanent liner assembly, with an aroma-tight seal.

BRIEF DESCRIPTION OF THE DRAWINGS

FIG. 3 is a cross-sectional view showing assembly of the container closure; and FIG. 4 shows the liner assemblies of FIG. 2, taken on an enlarged scale.

DETAILED DESCRIPTION OF THE PREFERRED EMBODIMENTS

Figure 1:
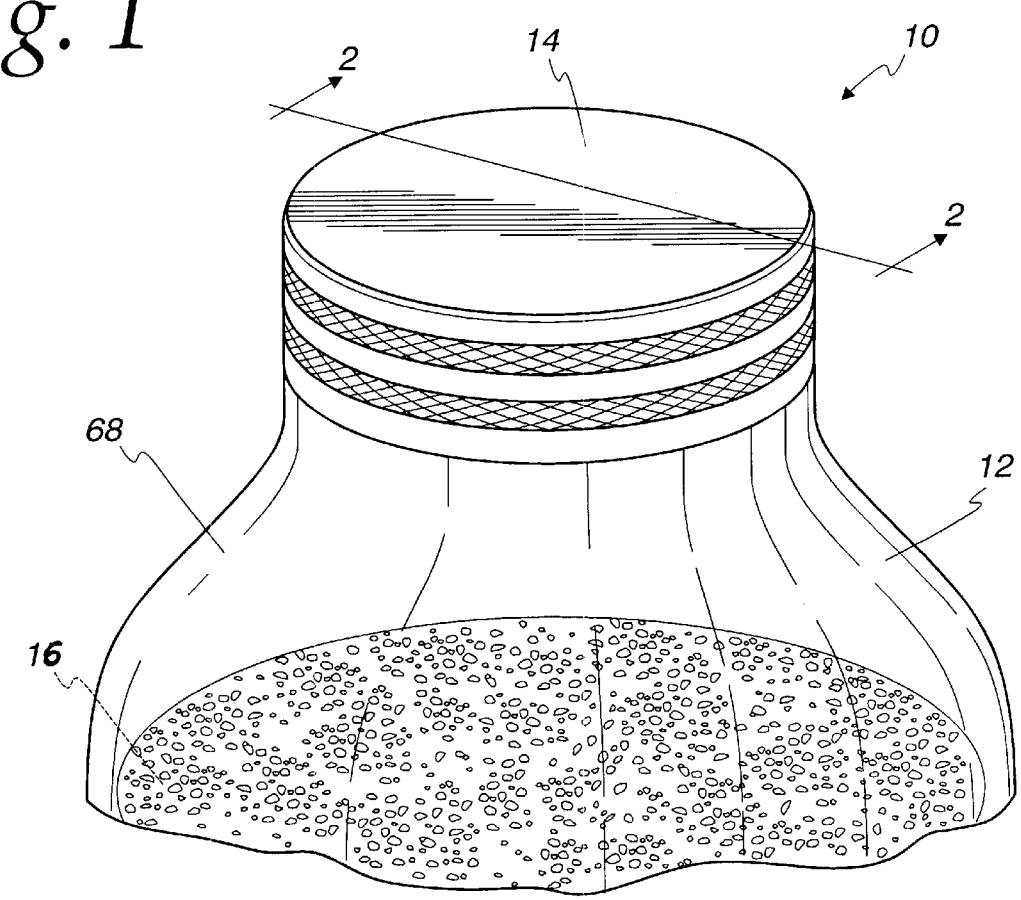
FIG. 1 is a perspective view of a container and closure according to principles of the present invention.

Turning now to the drawings, and initially to FIG. 1, a commercial food package is generally indicated at 10 and includes a container 12 having an upper opening through which product 16 is extracted by a consumer. As will be seen herein, the present invention has found commercial acceptance in the field of food packaging. Product 16, in the exemplary embodiment, comprises instant coffee, a food product with which consumers have associated an attractive fragrance. In the past, consumer experience with coffee involves handling freshly ground coffee beans which release a fragrance which consumers readily identify.

Due to the modern preparation of instant coffee granules, the aromatic content is sometimes not as strong as that associated with ground coffee beans. Accordingly, it is desirable to re-introduce the aroma, or volatile flavor experience which will enhance the ease and convenience offered by an instant food product. Heretofore, volatile flavor agents or aromatic fragrances have been introduced directly into the food product 16, usually at the time container 12 is filled. Thereafter, a closure 14 is applied to container 12 to seal the aromatic fragrance within the package 10. The present invention can be used with a wide variety of other types of closed containers. The drawings illustrate the popular type of container 12 having the form of a glass jar which has an upper threaded finish 18. A closure 14 in the form of a screw cap having internal threads 20 (see FIG. 2) is fitted to the threaded or screw finish 18 of container 12. In the past, a compressible gasket has been fitted to the interior of closure 14, being compressed by the upper end 22 of the container finish, with compression increasing as the screw engagement with the container is advanced.

Figure 2:
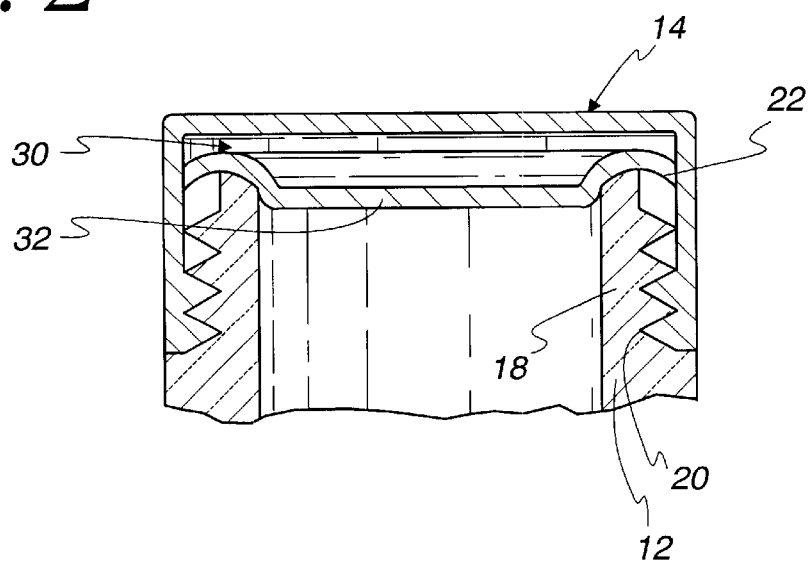
FIG. 2 is a cross-sectional view taken along the line 2—2 of FIG. 1.

Referring to FIGS. 2 and 4, the present invention employs two liner assemblies, including a permanent liner assembly 30 which, as will be seen, is associated with closure 14 and a removable liner assembly 32 associated with container 12.

Referring to FIG. 4, the liner assemblies 30, 32 preferably comprise a laminate composites with liner assembly 30 comprised of three layers and liner assembly 32 comprised of two layers. As will be seen herein, the layers comprising the liner assemblies 30, 32 are readily commercially available and can be fabricated in an inexpensive manner. Preferably, the permanent and releasable liner assemblies 30, 32 are joined together in the form of a composite sheet ready for a single die cutting step and subsequent mechanical insertion into the interior of closure 14, using conventional mass assembly techniques.

Referring to FIG. 3, closure 14 takes the form of a well known screw cap. Preferably, closure 14 is constructed of plastic material, in a conventional manner, so as to include a lid wall 36 and a sidewall 38 carrying a threaded portion 40 for engagement with the container finish. Closure 14 has an outer surface 42 and an inner surface 44. A pre-selected quantity of active compound, such as a volatile flavor agent 50, is placed on the interior surface of lid portion 36.

The present invention is also intended to apply to other types of active compounds which provide a volatile release of an agent beneficial to the product 16. Examples include concentrated consumable volatiles such as antioxidants, oxygen scavengers, carbon dioxide scavengers, nitrogen release agents (useful, for example, to prevent collapse of plastic containers) and oxygen-producing agents. With the present invention, small pouches of the above agents can be eliminated from consumer packaging.

The permanent liner assembly 30 is preferably die cut in the form of a disk dimensioned to fit within sidewall 38 of the closure, with a precision fit. The permanent liner assembly 30 is advanced in the direction of arrow 52 so as to engage or become closely spaced to the inner surface 44 of closure lid portion 36 and is then permanently secured to closure 14. Preferably, only the outer peripheral portion of the upper surface of liner assembly 30 is secured by a suitable adhesive to the inside surface of closure lid portion 36. This forms a small cavity or pocket for retaining the volatile flavor agent 50. As will be seen herein, liner assembly 30 is preferably joined to removable liner assembly 32 prior to die cutting and insertion in closure 14.

In the preferred embodiment, permanent liner assembly 30 includes a storage layer 60, preferably of a foam or porous polymer, compatible both physically and chemically with the active compound 50. Layer 60 comprises a polyolefin porous foam stock, preferably polypropylene. Layer 60 functions as a substrate for the storage of the active compound, which in the preferred embodiment, comprises a volatile flavor agent in the form of a flavor concentrate such as an essential oil. The oil saturates foam layer 60, diffusing through a layer of film 62 which is adhered to the upper surface of foam layer 60. Film layer 62 is disposed immediately adjacent the lid portion 36 of closure 14 and the volatile flavor agent 50. Preferably, film layer 62 comprises an extrusion coating of polyethylene film. A layer 64 of polypropylene material is applied by extrusion coating across the bottom surface of foam layer 60 and provides a controlled diffusion release of the active compound into the lower portion of closure 14 and (with additional reference to FIGS. 1 and 2) into the head space 68 above product 16.

Together, the film layers 62, 64 provide an overall controlled diffusion rate of the active compound exiting the permanent liner assembly. The rate of controlled release can be adjusted in part, by adjusting the solubility of the active compound within the matrix comprising the film layers 62, 64. In the preferred embodiment, the solubility of the active compound 50 is chosen with respect to polyethylene material of film layer 62 and of the polypropylene material of film layer 64. Control of the release rate also depends, in addition to the load parameters of the active compound, the thickness or film gauge of layers 62, 64. Preferably, the foam layer 60 does not play a significant role in limiting the diffusion rate of the active compound.

In addition to the polymeric materials described above for foam storage layer 60, matrices of organic material can also be employed, if desired. Examples include cellulose (especially in woven form), natural rubber and keratin. Support of such matrix is provided with enclosure between polyolefin film layers 62, 64. In this manner the desired matrix material is made suitable for conventional mass production handling.

As mentioned, the outer peripheral portion of the upper surface 68 of the permanent film assembly 30 (see FIG. 4) is adhesively secured to the inner surface 44 of closure lid portion 36. By applying a suitable adhesive to only the outer peripheral portion of surface 68, diffusion through the major portion of film layer 62 remains unimpeded and, accordingly, the active compound is allowed to freely diffuse into the foam storage layer 60. It is important that the adhesive joinder of the permanent liner assembly 30 to closure 14 cut off any escape path of active compound around the diffusion barrier system of permanent liner 30, as described above. As will be seen herein, tensile forces are applied to a bottom surface 72 of permanent liner assembly 30 and the adhesive joinder of assembly 30 to closure 14 is also chosen to withstand applied tensile forces, maintaining the controlled confinement of the active compound 50.

As a less preferred alternative, the outer side portion of permanent liner assembly 30 can be made to sufficiently engage the inner surface of closure sidewall 38 so as to prevent uncontrolled escape of the active compound between the permanent liner assembly 30 and the closure. Typically, a suitable adhesive material would be employed to secure the outer edge of assembly 30 to the inner surface of closure sidewall 38. However, this introduces practical commercial mass production difficulties. For example, while the adhesive (which provides sealing of the active compound) must not have substantial voids or gaps, it also must not intrude into the portion of the permanent liner assembly which engages the rim 22 of the container finish.

Turning to FIGS. 2 and 4, the removable liner assembly 32 includes a layer 80 of aluminum foil providing a diffusion barrier, effectively blocking diffusion of the active compound 50. Preferably, an upper surface 82 of layer 80 is coated with a releasable bonding agent, such as a peelable adhesive of wax or polymer material. In this manner, layers 64, 80 are releasably joined to one another, with an aroma-tight seal.

To aid in commercial fabrication of package 10, it is preferred that diffusion barrier layer 80 be secured to the rim 22 of the container finish, in the manner indicated in FIG. 2. Preferably, securement is accomplished by providing a bonding layer 86, chosen so as to provide a convenient securement to the upper end of container 12 after the container is filled with product 16 and closure 14 is threadingly engaged. Most preferably, layer 86 comprises a known induction sealable polyethylene film, which is extrusion coated to barrier layer 80. It is preferred that the polypropylene sealant receive a coating of a conventional induction sealable lacquer. After the package 10 is assembled and sealed, layer 86 is bonded to rim 22 using conventional induction sealing techniques.

As mentioned above, closure 14 is preferably constructed of lightweight, cost effective plastic material, although other materials, such as metal alloys, can be employed. A plastic material closure 14 is chosen with a number of design objectives in mind. For example, the plastic material must be suitable for threaded engagement with a container, and provide reliable repeated closing operations, as has been considered in the past. However, since the closure cooperates with permanent liner assembly 30 to form a cavity or pocket for confining active compound 50, consideration must be given to the compatibility of the plastic material with regard to any scalping of the active compound. In order to ensure that the active compound will be adequately confined so as to be available for subsequent controlled release, the inner surface 44 of closure 14 can be augmented with a high barrier coating such as PVDC or EVOH film.

A summary of the production steps to provide the flavor retention and release system of the present invention will now be described. Initially, and preferably at a remote location, a layer of foam polypropylene stock is extrusion coated with a polyolefin film on its major surfaces. Preferably, the upper surface is coated with a relatively thin polyethylene film and the bottom surface is coated with a thicker polypropylene film. The releasable liner assembly 32 is then fabricated by extrusion coating a layer of induction sealable polyethylene film on an aluminum foil sheet. The releasable and permanent liner assemblies are then peelably secured together to form a liner composite, using a wax or polymeric material. The resulting composite is then die cut to an appropriate dimension so as to be receivable in the interior of closure 14 with a controlled tolerance fit.

A pre-selected quantity of active compound is then applied to the interior of the closure lid. After application of a suitable adhesive to the outer peripheral portion of the upper surface of the liner composite, the liner composite is then inserted into the interior of the closure so as to form a pocket surrounding the active compound, and to effectively seal the outer periphery of the liner composite to the inner surface of the closure. If necessary, the inner surface of the cap is provided with a coating of diffusion barrier material to ensure retention of the active compound within the assembled closure and liner composite.

Next, the container is filled with product, such as instant coffee granules, to a pre-selected level within the container. Immediately prior to the threading engagement of the closure and container, a layer of induction sealable lacquer is applied to the exposed surface of the liner composite. Most preferably, only the outer peripheral portion of the exposed liner composite is coated with the induction sealable lacquer. The closure assembly with its liner composite is then threaded onto the container finish. Preferably, at this step, the diffusion barrier layer 80 and the foam storage layer 60 as well as intervening layers are compressed between the container rim 22 and the closure. Induction sealing energy is then applied to the package, with layer 86 thereby becoming bonded to the rim 22 of the container.

During packaging, distribution and storage, the active compound within the closure diffuses into the foam layer 50 as well as the surrounding film layers 62, 64. Equilibrium will be reached and maintained prior to first opening of the container, within the confined space defined by impression of rim 22 on the liner composite.

With delivery of the package, the consumer performs the first unscrewing action, opening the package. This causes the releasable liner assembly 32 to separate from the permanent liner assembly 30, with the rim 22 of container 12 retaining the removable liner assembly 32. The consumer then peels or otherwise removes the foil layer 80 from container 12, scooping the desired amount of product 16. The container is then re-closed by screwing the closure 14 with the attached permanent liner assembly 30, onto the container 12, creating a new head space between the upper surface of the product and the permanent liner assembly 30. Quickly thereafter, a new concentration gradient within the permanent liner assembly is established with diffusion of the active compound through the film layer 64. The active compound leaving the permanent liner assembly 30 is trapped in the head space between the permanent liner assembly and the upper surface of product 16, until the next opening of the package. In each subsequent opening of the package, the concentration of active compound in the head space is reduced, creating a new concentration gradient at the film interfaces of the permanent liner assembly. In this manner, active compound is transferred from the closure into the head space and continues with subsequent container openings as long as active compound remains in the foam storage layer.

As can be seen from the above, the present invention provides substantial advantages over prior art attempts to encapsulate volatile flavors or other active compounds in polymeric or natural organic food systems. With the present invention, previous difficulties in controlling the release of flavor upon opening of the container is overcome with protection offered by the barrier layer 80. Oxidation of the active component, which changes the performance profile of the active compound, is effectively prevented by film layer 64. Further, a preferential sorption of the volatile flavor components of the active compound is provided by active sites within storage layer 60.

Interaction of the liner composite with the head space in the container remaining after subsequent dispensing of product provides a renewed aroma impact upon subsequent opening. The strength and duration of the volatile flavor released in subsequent openings depends upon certain factors, many of which are readily controlled by the manufacturer. The amount of active compound (i.e., volatile flavor agent) at the initial assembly of the closure and liner composite is readily controllable. Another factor is the barrier, solubility, and diffusivity properties of the flavor agent through the closure walls. A further factor affecting aroma impact is the scalping of flavor volatiles by the polymer matrix of the closure. If necessary, a different polymer matrix and/or economical practical, barrier layers can be applied to the inner surface of the closure. As a further factor, the rate of permeation of the active compound through the film layers 62, 64, is determined by their thickness and diffusivity properties.

Several factors cannot be controlled by the manufacturer. For example, the time interval between subsequent openings by a consumer also affects the aroma impact, although this factor cannot be controlled by the package manufacturer. The amount of torque applied by the consumer to the closure rim in a re-closing step also affects the aroma impact, although this also cannot be controlled by the package manufacturer.

As mentioned, the present invention has found immediate commercial application in the field of instant coffee products. Several advantages are provided by the present invention over the prior practice of spraying volatile flavor agents directly into the product, during filling. The present invention provides a controlled and prolonged flavor aroma in the container head space throughout multiple opening and closing cycles. Assembly of the closure according to the present invention is accomplished with minimal incremental cost which uses conventional induction sealing techniques of the type employed with foam-based liners, and pre-treatment of the container, especially glass containers, is not required. If desired, the present invention may be readily employed with containers constructed of barrier polymeric materials (such as EVOH/polypropylene, or PET/EVOH material) rather than glass. If the quantity of active compound must be substantially increased for a particular commercial application, the closure can be readily modified to provide a sufficiently sized cavity for the increased active compound volume. For example, a depression can be formed in the lid portion of the closure. Finally, with a selection of other readily available film layer materials and storage layer materials, the present invention can be employed with a wide variety of products.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A flavor retention and release system for use with a container having an opening enclosed by a closure releasably engageable with said container, comprising:
    a permanent liner assembly dimensioned to be received in said closure, so as to cooperate therewith to form a pocket for retaining a volatile flavor agent;
    a permanent bond bonding at least a portion of said permanent liner assembly to said closure;
    a removable liner including a diffusion barrier impermeable with respect to said flavor agent;
    a container bond bonding said removable liner assembly to said container;
    a releasable bond, releasably bonding said removable liner assembly to said permanent liner assembly, with an aroma-tight seal; and
    said permanent liner assembly comprises a porous polypropylene foam layer having first and second opposed surfaces, each of which is extrusion coated with a polyolefin film layer diffusable with respect to said flavor agent.

2. A flavor retention and release system for use with a container having an opening enclosed by a closure releasably engageable with said container, comprising:
    a permanent liner assembly dimensioned to be received in said closure, so as to cooperate therewith to form a pocket for retaining a volatile flavor agent;
    a permanent bond bonding at least a portion of said permanent liner assembly to said closure;
    a removable liner including a diffusion barrier impermeable with respect to said flavor agent;
    a container bond bonding said removable liner assembly to said container;
    a releasable bond, releasably bonding said removable liner assembly to said permanent liner assembly, with an aroma-tight seal;
    said permanent liner assembly comprises a porous polypropylene foam layer having a thickness ranging between 30 and 34 mils, said porous polypropylene foam layer having a first surface extrusion coated with a polyethylene film of thickness approximately 0.5 mils and a second surface extrusion coated with a polyethylene film having a thickness of approximately 1.5 mils.

3. The flavor retention and release system according to claim 1 wherein said container bond comprises an induction sealable film.

4. The flavor retention and release system according to claim 3 wherein said induction sealable film comprises polyethylene.

5. The flavor retention and release system according to claim 4 wherein said induction sealable film has a thickness of approximately four mils.

6. The flavor retention and release system according to claim 1 wherein said removable liner diffusion barrier comprises aluminum foil.

7. The flavor retention and release system according to claim 6 wherein said aluminum foil has a thickness ranging between 0.6 and 0.8 mils.

8. The flavor retention and release system according to claim 1 wherein said releasable bond comprises a peelable adhesive.

9. The flavor retention and release system according to claim 1 wherein said permanent bonding comprises the step of bonding the outer periphery of said permanent liner assembly to said closure.

10. The flavor retention and release system according to claim 1 wherein said closure includes inner and outer surfaces, and said the flavor retention and release system further comprises a closure barrier layer on the inside surface of said closure, providing a diffusion barrier with respect to said flavor agent.

11. The method of retaining and releasing a volatile flavor agent upon repeated openings of a closed container, comprising the steps of:
    providing a container defining and opening for access to a container interior;
    providing a closure engageable with the container to close the opening, the closure having an inner surface;
    providing a permanent liner assembly dimensioned to be received in said closure;
    inserting said permanent liner assembly in said closure so as to form a pocket for retaining a volatile flavor agent;
    permanently bonding at least a portion of said permanent liner assembly to said closure;
    a removable liner assembly including a diffusion barrier impermeable with respect to said flavor agent;
    bonding said removable liner assembly to said container;
    releasably bonding said removable liner assembly to said permanent liner assembly, with an aroma-type seal; and
    the step of providing said permanent liner assembly comprises the step of providing a porous polypropylene foam layer having first and second opposed surfaces, and extrusion coating said first and said second opposed surfaces with a polyolefin film.

12. The method of retaining a releasing a volatile flavor agent upon repeated openings of a closed container, comprising the steps of:
    providing a container defining and opening for access to a container interior;
    providing a closure engageable with the container to close the opening, the closure having an inner surface;
    providing a permanent liner assembly dimensioned to be received in said closure;
    inserting said permanent liner assembly in said closure so as to form a pocket for retaining a volatile flavor agent;
    permanently bonding at least a portion of said permanent liner assembly to said closure;

a removable liner assembly including a diffusion barrier impermeable with respect to said flavor agent;

bonding said removable liner assembly to said container;

releasably bonding said removable liner assembly to said permanent liner assembly, with an aroma-type seal; and said step of providing a permanent liner assembly comprises the step of providing a porous polypropylene foam layer having a thickness ranging between 30 and 35 mils, said porous polypropylene foam layer having first and second opposed surfaces, extrusion coating said first surface with a polyethylene film having a thickness of approximately 0.5 mils, and extrusion coating said second opposed surface with a polyethylene film having a thickness of approximately 1.5 mils.

13. The method according to claim 11 wherein said step of permanently sealing said diffusion barrier to said container is carried out after said container is engaged with said closure.

14. The method according to claim 13 wherein said step of permanently sealing said diffusion barrier to said container comprises providing a sealing layer and bonding said sealing layer to said container using induction sealing techniques.

* * * * *